(12) United States Patent
Jungkamp et al.

(10) Patent No.: US 7,816,551 B2
(45) Date of Patent: Oct. 19, 2010

(54) METHOD FOR PRODUCING DINITRILES

(75) Inventors: Tim Jungkamp, Kapellen (BE); Robert Baumann, Mannheim (DE); Michael Bartsch, Neustadt (DE); Gerd Haderlein, Grünstadt (DE); Hermann Luyken, Ludwigshafen (DE); Jens Scheidel, Hirschberg (DE)

(73) Assignee: BASF Aktiengesellschaft (DE)

( * ) Notice: Subject to any disclaimer, the term of this patent is extended or adjusted under 35 U.S.C. 154(b) by 310 days.

(21) Appl. No.: 10/586,500

(22) PCT Filed: Jan. 27, 2005

(86) PCT No.: PCT/EP2005/000777
§ 371 (c)(1),
(2), (4) Date: Jul. 13, 2006

(87) PCT Pub. No.: WO2005/073172
PCT Pub. Date: Aug. 11, 2005

(65) Prior Publication Data
US 2007/0155978 A1 Jul. 5, 2007

(30) Foreign Application Priority Data
Jan. 29, 2004 (DE) .............. 10 2004 004 683

(51) Int. Cl.
*C07C 253/10* (2006.01)
(52) U.S. Cl. .................................. 558/338
(58) Field of Classification Search .............. 558/338
See application file for complete search history.

(56) References Cited

U.S. PATENT DOCUMENTS

| 3,496,215 | A | | 2/1970 | Drinkard et al. |
|---|---|---|---|---|
| 3,542,874 | A | | 11/1970 | Keizer et al. |
| 3,564,040 | A | | 2/1971 | Downing et al. |
| 3,752,839 | A | | 8/1973 | Drinkard, Jr. et al. |
| 3,766,241 | A | | 10/1973 | Drinkard |
| 3,773,809 | A | * | 11/1973 | Walter ................. 558/338 |
| 3,852,325 | A | | 12/1974 | King |
| 3,852,327 | A | | 12/1974 | Druliner et al. |
| 4,080,374 | A | | 3/1978 | Corn |
| 4,385,007 | A | | 5/1983 | Shook, Jr. |
| 5,723,641 | A | * | 3/1998 | Tam et al. ................. 556/13 |

FOREIGN PATENT DOCUMENTS

EP 0 464 691 1/1992

* cited by examiner

*Primary Examiner*—Joseph R Kosack
(74) *Attorney, Agent, or Firm*—Connolly Bove Lodge & Hutz

(57) ABSTRACT

An adiponitrile/methylglutaronitrile preparation process includes distilling a reaction stream to obtain stream 3 depleted in pentenenitriles (bottom product) and stream 4 enriched in pentenenitriles (top product); extracting stream 3 obtaining stream 6 enriched with extractant (top product) and stream 7 depleted in extractant (bottom product); distilling stream 6 obtaining stream 8 comprising the catalyst (bottom product) and stream 9 comprising the extractant (top product); distilling stream 7 obtaining stream 10 (bottom product) and stream 11 comprising the extractant (top product); distilling stream 10 obtaining stream 12 comprising catalyst degradation products, at least one promotor, adiponitrile and methylglutaronitrile (bottom product) and stream 13 comprising pentenenitriles (top product); distilling stream 12 obtaining stream 14 comprising catalyst degradation products and the promotor(s) (bottom product) and stream 15 comprising adiponitrile and methylglutaronitrile (top product); distilling stream 15 obtaining stream 16 comprising adiponitrile (bottom product) and stream 17 comprising methylglutaronitrile (top product).

17 Claims, 1 Drawing Sheet

METHOD FOR PRODUCING DINITRILES

RELATED APPLICATIONS

Figure 1:
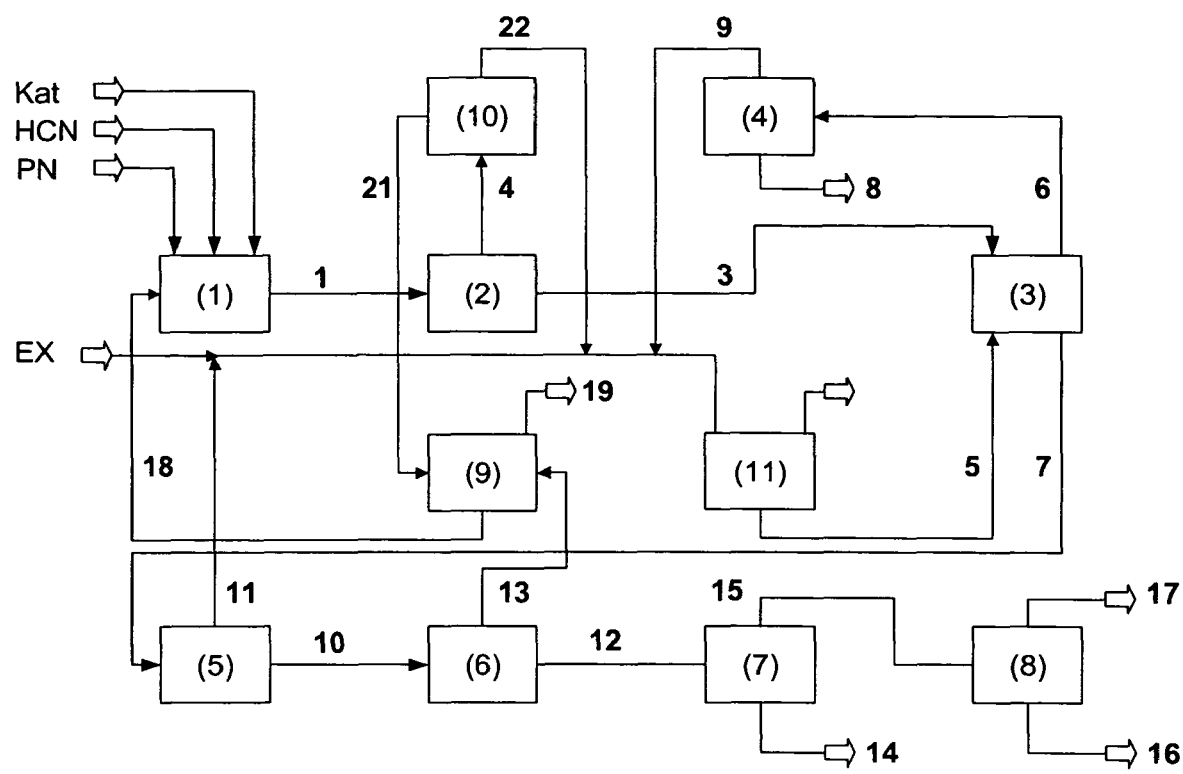

This application is a national stage application (under 35 U.S.C. 371) of PCT/EP2005/000777 filed Jan. 27, 2005, which claims benefit to German application 10 2004 004 683.2 filed Jan. 29, 2004.

DESCRIPTION

The present invention relates to a process for preparing adiponitrile and methylglutaronitrile A description of the essential features of a continuous process for preparing adiponitrile can be taken from U.S. Pat. No. 4,080,374, in which 1,3-butadiene, for example according to U.S. Pat. No. 3,496,215, is reacted with hydrogen cyanide to obtain a mixture comprising 3-pentenenitrile and 2-methyl-3-butenenitrile. 2-Methyl-3-butenenitrile may be isomerized, for example according to U.S. Pat. No. 3,542, 874, to 3-pentenenitrile. In a further step, the thus obtained 3-pentenenitrile, for example according to U.S. Pat. No. 3,752,839, is reacted with hydrogen cyanide to give a mixture comprising adiponitrile and methylglutaronitrile.

The known processes for preparing adiponitrile and methylglutaronitrile have a multitude of process steps. Individual process steps and configurations and improvements thereon have also already been discussed.

For example, U.S. Pat. Nos. 3,773,809 and 4,385,007 describe processes for extracting nickel(0) catalysts which are used in hydrocyanation processes from mixtures which comprise 3- and 4-pentenenitriles. A prerequisite is a conversion of more than 60% in the hydrocyanation. However, these degrees of conversion can be achieved only with great losses of nickel(0) catalysts.

The treatment of the streams obtained in the extraction is described in U.S. Pat. No. 4,080,374 which describes a process for working up hydrocyanation effluents by extraction, centrifugation of the raffinate and subsequent distillation in order to recover nitriles and the extractant from the adiponitrile-rich phase of the extraction. However, the necessity in this recovery of very substantially recovering the extractant and pentenenitrile from the catalyst stream in this recovery at industrially viable pressures results in the attainment of temperatures so high that they lead to at least partial decomposition of the product of value, adiponitrile, for example by reaction with the particular promoter used, zinc chloride or triphenylboron.

With regard to the workup of reaction effluents of the hydrocyanation of pentenenitrile to adiponitrile with recycling of unconverted pentenenitrile, U.S. Pat. No. 3,564,040 should also be mentioned, which describes the removal of trans-2-pentenenitrile from a mixture of cis-, trans-3-pentenenitriles and 4-pentenenitriles by catalytic isomerization of the trans-2-pentenenitrile to cis-2-pentenenitrile. The isomerization is followed by a fractional distillation to remove cis-2-pentenenitrile and a recycling of the pentenenitrile stream with the remaining trans-2-pentenenitrile which is isomerized in the reactor to cis-2-pentenenitrile. It is evident from the examples of U.S. Pat. No. 3,564,040 that there is poisoning of the catalysts for the hydrocyanation even by 2.5% by weight of trans-2-pentenenitrile.

With regard to the removal of cis-2-pentenenitriles from mixtures of 3- and 4-pentenenitriles, U.S. Pat. Nos. 3,852,325 and 3,852,327 should be mentioned, which describe the isomerization of trans-2-pentenenitrile with triarylboron halide or nickel(0) with tritolyl phosphite ligands with addition of Lewis acid in order to convert trans-2-pentenenitrile to cis-2-pentenenitrile which can be more readily removed from 3-pentenenitriles.

The workup of adiponitrile is described in U.S. Pat. No. 3,766,241, which relates to the workup of hydrocyanation effluents by treating them with ammonia, in order to precipitate zinc(II) chloride, which is used in the hydrocyanation as a promoter, as the ammonia adduct.

The individual process steps known hitherto which are necessary to isolate adiponitrile from a hydrocyanation mixture and recycle unconverted pentenenitrile and the nickel(0) catalyst into the process to avoid feedstock losses lead to unsatisfactory results as a result of product of value and catalyst losses.

Accordingly, it is an object of the present invention to provide an integrated process for preparing adiponitrile and methylglutaronitrile which substantially avoids the disadvantages of the prior art discussed above and preferably exhibit the advantages cited hereinbelow.

This object is achieved by the process according to the invention for preparing adiponitrile and methylglutaronitrile.

The process according to the invention is characterized by the following process steps:

(a) reacting a reactant stream comprising pentenenitriles with hydrogen cyanide in the presence of at least one catalyst and of at least one promoter to obtain a reaction stream which comprises pentenenitriles, the at least one catalyst, catalyst degradation products, the at least one promoter, adiponitrile and methylglutaronitrile, (b) distilling the reaction stream to obtain a stream 3 which is depleted in pentenenitriles and comprises the at least one catalyst, catalyst degradation products, the at least one promoter, adiponitrile and methylglutaronitrile as the bottom product and a stream 4 enriched in pentenenitriles as the top product, (c) extracting the stream 3 using an extractant present in stream 5 to obtain a stream 6 enriched with extractant as the top product which comprises the catalyst, and a stream 7 depleted in extractant as the bottom product which comprises catalyst degradation products, the at least one promoter, pentenenitriles, adiponitrile and methylglutaronitrile, (d) distilling the stream 6 to obtain a stream 8 comprising the catalyst as the bottom product and a stream 9 comprising the extractant as the top product, (e) distilling the stream 7 to obtain a stream 10 as the bottom product which comprises catalyst degradation products, the at least one promoter, pentenenitriles, adiponitrile and methylglutaronitrile, and a stream 11 comprising the extractant as the top product, (f) distilling the stream 10 to obtain a stream 12 as the bottom product which comprises catalyst degradation products, the at least one promoter, adiponitrile and methylglutaronitrile, and a stream 13 comprising pentenenitriles as the top product, (g) distilling the stream 12 to obtain a stream 14 as the bottom product which comprises catalyst degradation products and the at least one promoter, and a stream 15 as the top product which comprises adiponitrile and methylglutaronitrile, (h) distilling the stream 15 to obtain a stream 16 comprising adiponitrile as the bottoms and a stream 17 comprising methylglutaronitrile as the top product.

In process stage (a), a reactant stream which comprises pentenenitriles is reacted with hydrogen cyanide in the presence of at least one catalyst and of at least one promoter to obtain a reaction stream which comprises pentenenitriles, the at least one catalyst, catalyst degradation products, the at least one promoter, adiponitrile and methylglutaronitrile. A further constituent of the reaction stream is valeric acid.

The reactant stream used in this case preferably stems from the homogeneous hydrocyanation of butadiene in the presence of a nickel(0) catalyst which is known per se from the prior art.

The catalysts used in process step (a) are preferably nickel (0)-phosphorus ligand complexes.

The Ni(0) complexes which contain phosphorus ligands and/or free phosphorus ligands are preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I $$P(X^1R^1)(X^2R^2)(X^3R^3) \tag{I}$$

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1 R^2 R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified in this description.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula Ia

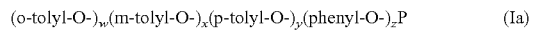

(o-tolyl-O-)$_w$(m-tolyl-O-)$_x$(p-tolyl-O-)$_y$(phenyl-O-)$_z$P  (Ia)

where w, x, y, z are each a natural number and the following conditions apply: w+x+y+z=3 and w, z≦2.

Such compounds Ia are, for example, (p-tolyl-O-)(phenyl-O-)$_2$P, (m-tolyl-O-)(phenyl-O-)$_2$P, (o-tolyl-O-)(phenyl-O-)$_2$P, p-tolyl-O-)$_2$(phenyl-O-)P, (m-tolyl-O-)$_2$(phenyl-O-)P, (o-tolyl-O-)$_2$(phenyl-O-)P, (m-tolyl-O-)(p-tolyl-O-)(phenyl-O-)P, (o-tolyl-O-)(p-tolyl-O-)(phenyl-O-)P, (o-tolyl-O-)(m-tolyl-O-)(phenyl-O-)P, (p-tolyl-O-)$_3$P, (m-tolyl-O-)(p-tolyl-O-)$_2$P, (o-tolyl-O-)(p-tolyl-O-)$_2$P, (m-tolyl-O-)(p-tolyl-O-)$_2$P, (o-tolyl-O-)$_2$(p-tolyl-O-)P, (o-tolyl-O-)(m-tolyl-O-)(p-tolyl-O-)P, (m-tolyl-O-)$_3$P, (o-tolyl-O-)(m-tolyl-O-)$_2$P (o-tolyl-O-)$_2$(m-tolyl-O-)P or mixtures of such compounds.

Mixtures comprising (m-tolyl-O-)$_3$P, (m-tolyl-O-)$_2$(p-tolyl-O-)P, (m-tolyl-O-)(p-tolyl-O-)$_2$P and (p-tolyl-O-)$_3$P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula Ib:

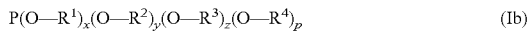

$$P(O\text{---}R^1)_x(O\text{---}R^2)_y(O\text{---}R^3)_z(O\text{---}R^4)_p \tag{Ib}$$

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y,z,p: each independently 0, 1 or 2, with the proviso that x+y+z+p=3.

Preferred phosphites of the formula Ib can be taken from DE-A 199 53 058. The $R^1$ radical may advantageously be o-tolyl, o-ethylphenyl, o-n-propylphenyl, o-isopropyl-phenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The R⁴ radical is preferably phenyl. p is preferably zero. For the indices x, y, z and p in compound Ib, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula Ib are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula Ib are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula Ib may be obtained by a) reacting a phosphorus trihalide with an alcohol selected from the group consisting of $R^1OH$, $R^2OH$, $R^3OH$ and $R^4OH$ or mixtures thereof to obtain a dihalophosphorous monoester,
b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and
c) reacting the monohalophosphorous diester mentioned with an alcohol selected from the group consisting of $R^1OH$, $R^2OH$, $R^3OH$ and $R^4OH$ or mixtures thereof to obtain a phosphite of the formula Ib.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites Ib and for the workup can be taken from DE-A 199 53 058.

The phosphites Ib may also be used in the form of a mixture of different phosphites Ib as a ligand. Such a mixture may be obtained, for example, in the preparation of the phosphites Ib.

However, preference is given to the phosphorus ligand being multidentate, in particular bidentate. The ligand used therefore preferably has the formula II

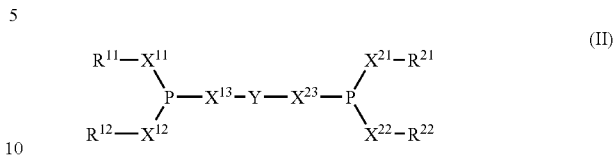

where
$X^{11}, X^{12}, X^{13}, X^{21}, X^{22}, X^{23}$ are each independently oxygen or a single bond
$R^{11}, R^{12}$ are each independently identical or different, separate or bridged organic radicals
$R^{21}, R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is advantageously an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be the same or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals too may each be separate or bridged. The $R^{11}$, $R^{12}$, $R^{21}$ and $R^{22}$ radicals may each be separate, two may be bridged and two separate, or all four may be bridged, in the manner described. In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of 10.30.2003 which has an earlier priority date but had not been published at the priority date of the present application.

The compounds I, Ia, Ib and II described and their preparation are known per se. Phosphorus ligands used may also be a mixture comprising at least two of the compounds I, Ia, Ib and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula Ib

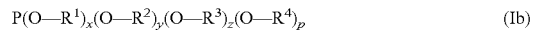

$$P(O-R^1)_x(O-R^2)_y(O-R^3)_z(O-R^4)_p \qquad (Ib)$$

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that $x+y+z+p=3$; and mixtures thereof.

Process step (a) of the process according to the invention is preferably carried out at an absolute pressure of from 0.1 to 10 bar, more preferably from 0.5 to 2 bar, in particular from 0.8 to 1.5 bar. the temperature in process step (a) is preferably from 40 to 150° C., more preferably from 50 to 100° C., in particular from 60 to 70° C.

Process step (a) may be carried out in any suitable apparatus known to those skilled in the art. Examples of suitable reactors are those having backmixing characteristics.

In the hydrocyanation of process step (a), there may be partial decomposition of the catalysts. The decomposition products resulting therefrom are, for example, nickel(II) cyanide-containing components. Further degradation products formed are, for example, hydrolyzed phosphorus compounds which are derived by reaction of the particular substances I and II used as a result of traces of water which may be present in the feedstocks, especially in the hydrogen cyanide used. Further degradation products formed are oxidized phosphorus compounds which are derived by reaction of the particular substances I and II used to give compounds having phosphorus atoms in the oxidation state (V), as a result of reaction with elemental oxygen or as a result of reaction with peroxides which may be present in the feedstocks, especially as a result of leakage in the apparatus or by dissolution of oxygen in pentenenitrile, for example in the course of storage, with subsequent formation of peroxide compounds of the pentenenitriles. Further degradation products formed, especially of the chelate ligands II used, may, under disadvantageous conditions, be monodentate degradation products which are derived, for example, by thermally induced, or proton- or base-catalyzed, rearrangement of the radicals on the phosphorus atoms of the particular structures and have less hydrocyanation activity than the starting materials.

In the hydrocyanation of process step (a), 2-pentenenitriles are generally formed additionally and are catalyst poisons when nickel(0) catalysts with monodentate ligands such as $ZnCl_2$ or $BPh_3$ are used as the promoter.

The promoter which is used in process step (a) of the process according to the invention is preferably selected from the group consisting of the Lewis acids $ZnCl_2$, $FeCl_2$, $Et_2AlCl$, $Et_3Al_2Cl_3$, $EtAlCl_2$ and $BPh_3$.

Process step (a) may be carried out in any suitable apparatus known to those skilled in the art. Useful apparatus for the reaction is that which is customary for this purpose, as described, for example, in: Kirk-Othmer, Encyclopedia of Chemical Technology, 4th Ed. Vol. 20, John Wiley & Sons, New York 1996, pages 1040 to 1055, such as stirred tank reactors, loop reactors, gas circulation reactors, bubble column reactors or tubular reactors, in each case if appropriate with apparatus to remove heat of reaction. The reaction may be carried out in a plurality of, such as two or three, apparatuses.

In process step (b), the reaction stream is distilled to obtain a stream 3 depleted in pentenenitriles as the bottom product which comprises the at least one catalyst, catalyst degradation products, the at least one promoter, adiponitrile and methylglutaronitrile, and a stream 4 enriched in pentenenitriles as the top product.

A substantial removal of the pentenenitriles before the subsequent extraction in process step (c) is advantageous, since phase separation in the extraction is otherwise sometimes complicated or prevented, and the efficiency of the extraction of catalyst constituents from the hydrocyanation effluent is adversely affected by high pentenenitrile concentration.

The evaporation of process step (b) may be effected in one stage or in a plurality of stages performed in series at different temperatures and pressures. In addition, the evaporator stage of process step (b) may be designed as a distillation column, in which case operation as a rectifying or stripping column is possible. In a preferred embodiment, the evaporator stage (b) is operated as a distillation column in stripping mode.

In a further preferred embodiment of the process according to the invention, at least one of the evaporator stages of process step (b) is operated with a divided column bottom, in which case the circulation stream which is generally large relative to the bottom draw stream is conducted from a first column bottom of the evaporator stage in question to the evaporator, the liquid effluent stream from the evaporator is not returned directly to the column bottom, but rather collected in a second column bottom which is separated from the first column bottom, the bottom draw stream is obtained from the second column bottom and the remaining excess of evaporator circulation stream is allowed to overflow into the first column bottom, and the bottom draw stream obtained from the second column bottom is a mixture which is depleted in low boilers compared to the draw from the first column bottom.

The absolute pressure in process step (b) is preferably from 0.001 to 1 bar, more preferably from 0.005 to 0.1 bar, in particular from 0.01 to 0.05 bar. The distillation is carried out in such a way that the temperature in the bottom of the distillation apparatus is preferably from 40 to 180° C., more preferably from 70 to 120° C., in particular from 80 to 100° C. The distillation is carried out in such a way that the temperature at the top of the distillation apparatus is preferably from −15 to 150° C., more preferably from 0 to 60° C., in particular from 20 to 50° C. In a particularly preferred embodiment of the process according to the invention, the temperature ranges specified above are maintained both at the top and in the column bottom.

The stream 4 enriched in pentenenitriles in process step (b) generally comprises trans-3-pentenenitrile, cis-3-pentenenitrile, 4-pentenenitrile, cis-2-pentenenitrile, trans-2-pentenenitrile and (E)-2-methyl-2-butenenitrile. In a particularly preferred embodiment, this stream 4 is distilled at least partly in a further process step (i) to obtain a stream 18 depleted in cis-2-pentenenitrile and (E)-2-methyl-2-butenenitrile, and a stream 19 enriched in cis-2-pentenenitrile and (E)-2-methyl-2-butenenitrile. The stream 18 depleted in cis-2-pentenenitrile and (E)-2-methyl-2-butenenitrile is preferably recycled into the hydrocyanation of process step (a). Stream 19 may be fed to a further workup in order to recover product of value by isomerizing the cis-2-pentenenitrile to 3-pentenenitrile, for example according to a process as described in DE 103 23 803 or in DE-A-102 004 004 716.

The distillation of the optional process step (i) may be carried out in any suitable apparatus known to those skilled in the art. The distillation of process step (i) takes place preferably in one or more distillation columns. The columns may be equipped with one or more side draws. The internals used for the distillation columns are preferably structured sheet metal packings, structured fabric packings, bubble-cap trays, dual-flow trays or beds of random packings or combinations of two or more of these classes of separating internals.

One or more columns of process step (i) may be designed as a dividing wall column with side draw. The columns of process step (i) may be equipped with a falling-film evaporator, thin-film evaporator, natural circulation evaporator or forced circulation-decompression evaporator as the evaporator unit.

The absolute pressure in process step (i) is preferably from 0.01 to 10.0 bar, more preferably 0.05 to 5.0 bar, in particular 0.1 to 1.0 bar. The distillation is carried out in such a way that the temperature in the bottom of the distillations apparatus is preferably from 40 to 250° C., more preferably from 50 to 180° C., in particular from 60 to 150° C. The distillation is carried out in such a way that the temperature at the top of the distillation apparatus is preferably from 0 to 200° C., more preferably from 15 to 180° C., in particular from 20 to 150° C. In a particularly preferred embodiment of the process according to the invention, the aforementioned temperature ranges in the optional process step (i) are maintained both at the top and in the bottom.

According to the invention, it has been found that, in contradiction to the prior art, 2-pentenenitriles do not constitute catalyst poisons when the hydrocyanation is carried out using nickel(0) catalysts with chelate ligands. It is therefore unnecessary to fully remove cis-2-pentenenitrile and (E)-2-methyl-2-butenenitrile from the stream 18 recycled into the hydrocyanation when a nickel(0) catalyst with chelate ligands is used in the hydrocyanation of process step (a).

The stream 3 depleted in pentenenitrile in process step (b) still contains preferably from 0.1 to 90% by weight, more preferably from 1 to 50% by weight, in particular from 5 to 30% by weight, of pentenenitriles. These pentenenitriles are generally composed of cis-3-pentenenitrile, trans-3-pentenenitrile and 4-pentenenitrile, and also additionally, each having a proportion of preferably less than 20% by weight, more preferably less than 10% by weight, of cis-2-pentenenitrile, trans-2-pentenenitrile, (E)-2-methyl-2-butenenitrile and (Z)-2-methyl-2-butenenitrile. Further constituents are the by-products formed in the hydrocyanation to a minor extent, for example valeronitrile.

In process step (c), the stream 3 is extracted using an extractant in stream 5 to obtain a stream 6 enriched with extractant as the top product which comprises at least one catalyst, and a stream 7 depleted in extractant which comprises catalyst degradation products, the at least one promoter, pentenenitriles, adiponitrile and methylglutaronitrile.

Process step (c) may be carried out in any suitable apparatus known to those skilled in the art. The extraction of process step (c) preferably takes place in countercurrent extraction columns, mixer-settler units or combinations of mixer-settler units with columns. Particular preference is given to using countercurrent extraction columns which are equipped in particular with sheet metal packings as dispersing elements. This is surprising since the hydrocyanation effluent is laden with solids. According to the invention, it has been found that the nickel(II) cyanide-containing solid which is formed in the hydrocyanation step (a), contrary to expectations, does not have a tendency to accumulate under the conditions in the extraction and does not form any noticeable deposits on column internals.

In a further particularly preferred embodiment, the countercurrent extraction is performed in a compartmented, stirred extraction column.

In a preferred embodiment, the extractant is used as a disperse phase, the bottom effluent obtained in process step (b) or the effluent from the hydrocyanation in process step (a) as a continuous phase.

In the extraction, a phase ratio of from 0.1 to 10, calculated as the ratio of volume of the extractant supplied to volume of the mixture to be extracted is used. In a preferred embodiment, the extraction is operated with a phase ratio of from 0.4 to 2.5, in a preferred embodiment at from 0.75 to 1.5.

The absolute pressure in process step (c) is preferably from 0.1 to 10 bar, more preferably from 0.5 to 5 bar, in particular from 1.0 to 2.5 bar. The extraction is preferably carried out at temperatures of from −15 to 120° C., more preferably from 0 to 60° C., in particular from 25 to 45° C.

In a preferred embodiment of the present invention, the extractant is selected from the group consisting of cyclohexane, methylcyclohexane, n-hexane, n-heptane, isomeric C6, C7, C8, C9 cycloaliphatics, isomeric C6, C7, C8, C9 isoaliphatics, cis-, trans-decahydronaphthalene and mixtures thereof.

In a particularly preferred embodiment, the extractant used is cyclohexane or methylcyclohexane or n-heptane.

The extractant used is preferably anhydrous, anhydrous meaning in the context of the present invention that the extractant contains less than 100 ppm, preferably less than 50 ppm, in particular less than 10 ppm, of water. The extractant may be dried by suitable processes known to those skilled in the art, for example by adsorption or azeotropic distillation.

The extractant is preferably dried by azeotropic distillation in a separate process step (j). This is preferably effected distillatively as a heteroazeotropic distillation. The absolute pressure in this process step (j) is preferably from 0.01 to 10.0 bar, more preferably from 0.05 to 5.0 bar, in particular from 0.1 to 1.0 bar. The distillation is carried out in such a way that the temperature in the bottom of the distillation apparatus is preferably from 40 to 250° C., more preferably from 50 to 180° C., in particular from 60 to 150° C. The distillation is carried out in such a way that the temperature at the top of the distillation apparatus is preferably from 0 to 200° C., more preferably from 5 to 100° C., in particular from 20 to 50° C. In a particularly preferred embodiment of the process according to the invention, the aforementioned temperature ranges are maintained both at the top and in the bottom of the distillation apparatus.

The azeotropic distillation of the extractant is preferably effected in a distillation column having in particular bubble-cap trays, structured sheet metal packings, structured fabric packings, dual-flow trays or beds of random packings as separating internals, if appropriate in a dividing wall column having side draws present if appropriate, a phase separator at the liquid draw of the top condenser to remove water, with apparatus for separate recycling of organic phases as reflux to columns, and also further apparatus suitable for azeotropic distillation.

In process step (d), a distillation of stream 6 takes place to obtain a stream 8 comprising the at least one catalyst and a stream 9 comprising the extractant.

This process step serves substantially to recover the catalyst and the extractant.

Process step (d) may be carried out in any suitable apparatus known to those skilled in the art. The distillation of process step (d) preferably takes place in one or more evaporator stages and also distillation columns.

Useful internals for the distillation columns are preferably structured sheet metal packing, structured fabric packing, bubble-cap trays, dual-flow trays or beds of random packings or combinations of two or more of these classes of separating internals. The distillation column of process step (d) may be designed with one or more liquid or gaseous side draws. The distillation column from process step (d) may be designed as a dividing wall column having one or more gaseous or liquid side draws present.

The one or more evaporator stages or the distillation column of process step (d) may in particular be equipped with falling-film evaporators, thin-film evaporators, natural circulation evaporators, forced circulation-decompression evaporators and multiphase helical tube evaporators.

In a further embodiment of the process according to the invention, at least one of the evaporator units of process step (d) is operated with a divided column bottom, in which case the circulation stream which is generally large relative to the bottom draw stream is conducted from a first column bottom of the evaporator stage in question to the evaporator, the liquid effluent stream from the evaporator is not returned directly to the column bottom, but rather collected in a second column bottom which is separated from the first column bottom, the bottom draw stream is obtained from the second column bottom and the remaining excess of evaporator circulation stream is allowed to overflow into the first column bottom, and the bottom draw stream obtained from the second column bottom is a mixture which is depleted in low boilers compared to the draw from the first column bottom.

The absolute pressure in process step (d) is preferably from 0.001 to 2.0 bar, more preferably from 0.01 to 0.5 bar, in particular from 0.09 to 0.12 bar. The distillation is carried out in such a way that the temperature in the bottom of the distillation apparatus is preferably from 40 to 150° C., more preferably from 70 to 120° C., in particular from 80 to 100° C. The distillation is carried out in such a way that the temperature at the top of the distillation apparatus is preferably from −15 to 100° C., more preferably from 0 to 60° C., in particular from 20 to 50° C. In a particularly preferred embodiment of the process according to the invention, the temperature ranges specified above are maintained both at the top and in the column bottom.

In the removal of the extractant to recover the catalyst in process step d), in a preferred embodiment of the present invention, 3-pentenenitrile is added to the distillation as an intermediate boiler. One advantage of this solvent change is that effective depletion of the extractant from the high-boiling catalyst stream is possible at evaporator temperatures which are low enough not to thermally damage the particular nickel catalyst used and especially the chelate ligand, although the pressure is still high enough to be able to condense the extractant having a comparatively low boiling point in comparison to the catalyst constituents at the top of the evaporator stage or distillation column even at customary cooling water temperatures of from 25 to 50° C. The solvent change additionally has the advantage that the flowability and monophasicity of the catalyst solution is ensured, since, depending on the temperature and residual content of extractant, catalyst constituents may in some cases crystallize out without the addition of 3-pentenenitrile. 3-Pentenenitrile, which, depending on the pressure conditions, can only be removed fully with difficulty, for example from the cyclohexane or methylcyclohexane extractants, or, owing to minimum vapor pressure azeotrope formation, cannot be removed fully at all, does not have a disruptive effect on the process according to the invention at a proportion of preferably up to 10% by weight, more preferably up to 5% by weight, in particular up to 1% by weight, based on the total amount of the extractant feed stream to the extraction column in process step (c).

In a preferred embodiment of the process according to the invention, the stream 9 obtained in process step (d) and comprising the extractant is recycled at least partly into the extraction step (c). The recycled stream 9 is preferably dried before the extraction step (c), for example in the above-described process step (j), so that the water content in this stream is preferably less than 100 ppm, more preferably less than 50 ppm, in particular less than 10 ppm.

In a further preferred embodiment of the process according to the invention, the stream 8 obtained in process step (d) and comprising the catalyst is recycled at least partly into the hydrocyanation of process step (a). In a preferred embodiment of the process according to the invention, the proportion of extractant in stream 8 is preferably less than 10% by weight, more preferably less than 5% by weight, in particular less than 1% by weight, based on the total amount of stream 8.

Since the removal of the extractant from the catalyst is thus not necessarily quantitative, it may be the case that extractant still present in stream 8 is likewise recycled into the hydrocyanation stage. This extractant is then transferred in the downstream, above-described process stage (b) substantially into stream 4 comprising pentenenitriles, and accumulates there. If extractant will get into stream 4, it is thus advantageous to free this stream 4 of the extractant in a further process step (k) by distillation. Process step (k) may be carried out in any suitable apparatus known to those skilled in the art. The distillation of process step (k) preferably takes place in one or more distillation columns. Useful internals for the distillation columns are preferably structured sheet metal packings, structured fabric packings, bubble-cap trays, dual-flow trays or beds of random packings or combinations of two or more of these classes of separating internals. The distillation column of process step (k) may be designed with one or more liquid or gaseous side draws. The distillation column from process step (d) may be designed as a dividing wall column having one or more gaseous or liquid side draws present.

This forms the streams 21, comprising pentenenitrile, and 22, comprising the extractant. The stream 21 is preferably recycled into the above-described process step (i) to be carried out if appropriate, in order to free the stream of any cis-2-pentenenitrile and (E)-2-methyl-2-butenenitrile present. The stream 22 comprising the extractant is preferably recycled into the extraction of process step (c).

In a preferred embodiment of the process according to the invention, the thus obtained stream 22 comprising the extractant is recycled at least partly into the extraction step (c). The recycled stream 22 is preferably dried before the extraction step (c), for example in the above-described process step (j), so that the water content in this stream is preferably less than 100 ppm, more preferably less than 50 ppm, in particular less than 10 ppm.

In a further embodiment, streams 9 and 22 are dried before they are recycled into the extraction of process step (c), if appropriate in an apparatus.

The absolute pressure in the optional process step (k) is preferably from 0.01 to 10.0 bar, more preferably from 0.05 to 5.0 bar, in particular from 0.1 to 1.0 bar. The distillation is carried out in such a way that the temperature in the bottom of the distillation apparatus is preferably from 40 to 250° C., more preferably from 50 to 180° C., in particular from 60 to 150° C. The distillation is carried out in such a way that the temperature at the top of the distillation apparatus is preferably from 0 to 200° C., more preferably from 15 to 180° C., in particular from 20 to 150° C. In a particularly preferred embodiment of the process according to the invention, the aforementioned temperature ranges are maintained both at the top and in the bottom of the distillation apparatus.

In process step (e), a distillation of stream 7 takes place to obtain a stream 10 as the top product which comprises catalyst degradation products, the at least one promoter, pentenenitriles, adiponitrile and methylglutaronitrile, and a stream 11 comprising the extractant as the top product.

The process step (e) may carried out in any suitable apparatus known to those skilled in the art. The distillation of process step (e) preferably takes place in one or more evaporator stages or one or more distillation columns. Useful internals for the distillation columns are preferably structured sheet metal packing, structured fabric packing, bubble-cap trays, dual-flow trays or beds of random packings or combinations of two or more of these classes of separating internals. The distillation column of process step (e) may be designed with one or more liquid or gaseous side draws. The distillation column from process step (e) may be designed as a dividing wall column having one or more gaseous or liquid side draws present.

The evaporator units for the one or more evaporator stages or one or more distillation columns may in particular be equipped with falling-film evaporators, thin-film evaporators, natural circulation evaporators, forced circulation-decompression evaporators and multiphase helical tube evaporators.

In a preferred embodiment of the process according to the invention, at least one of the one or more evaporator units of process step (e) is operated with a divided column bottom, in which case the circulation stream which is generally large relative to the bottom draw stream is conducted from a first column bottom of the evaporator stage in question to the evaporator, the liquid effluent stream from the evaporator is not returned directly to the column bottom, but rather collected in a second column bottom which is separated from the first column bottom, the bottom draw stream is obtained from the second column bottom and the remaining excess of evaporator circulation stream is allowed to overflow into the first column bottom, and the bottom draw stream obtained from the second column bottom is a mixture which is depleted in low boilers compared to the draw from the first column bottom.

The absolute pressure in process step (e) is preferably from 0.1 to 10.0 bar, more preferably from 0.5 to 5.0 bar, in particular from 0.15 to 0.2 bar. The distillation is carried out in such a way that the temperature in the bottom of the distillation apparatus is preferably from 40 to 250° C., more preferably from 50 to 200° C., in particular from 100 to 180° C. The distillation is carried out in such a way that the temperature at the top of the distillation apparatus is preferably from −15 to 150° C., more preferably from 0 to 60° C., in particular from 20 to 50° C. In a particularly preferred embodiment of the process according to the invention, the temperature ranges specified above are maintained both at the top and in the column bottom.

The stream 11 comprising the extractant is preferably recycled into the extraction of process step (c). Preference is given to drying stream 11 before it is recycled into the extraction of process step (c), so that the water content in these streams is preferably less than 100 ppm, more preferably less than 50 ppm, in particular less than 10 ppm. This may be effected, for example, in process step (j).

In a preferred embodiment A of the process according to the invention, the distillation in process step (e) is carried out in such a way that the resulting stream 10 contains less than 10% by weight, more preferably less than 1% by weight, in particular less than 0.1% by weight, of extractant.

In a further preferred embodiment B of the process according to the invention, the stream 11 comprises less than 10% by weight, more preferably less than 5% by weight, in particular less than 2% by weight, of pentenenitriles.

In a particularly preferred embodiment C, the specifications of embodiment A and B are achieved.

In a further preferred embodiment D of the process according to the invention, the distillation in process step (e) is carried out in such a way that the resulting stream 10 contains less than 10% by weight, more preferably less than 5% by weight, in particular less than 1% by weight, of pentenenitriles. If this specification of stream 10 is achieved, it is possible to conduct stream 10 directly into process step (g) with exclusion of process step (f). This specification is preferably achieved by using, in process step (e), a combination, adapted to the temperature-dependent vapor pressure of pentenenitrile, of evaporation temperature and distillation pressure, so that pentenenitriles are distinctly depleted via the bottom and a mixture of pentenenitrile and the particular extractant used is obtained overhead. In a preferred embodiment, this mixture of substances having noticeably different condensation points is condensed in a process for closed condensation. The closed condensation allows the stream 11 to be condensed fully at distinctly higher temperatures in comparison to the customary open condensation, or a distinctly lower column pressure in comparison to the open condensation at the same cooling medium temperature, and thus a lower content of low boilers in the bottom draw stream at the same bottom temperature, to be attained. This embodiment has the result that a distillation stage for recycling pentenenitriles from stream 7 can be dispensed with.

The magnitude of the contents of pentenenitriles typically found in stream 7 after the extraction makes necessary a removal and extraction for the economic practice of the process. The closed condensation may be performed in all further ways suitable and known to those skilled in the art. One suitable embodiment is to carry out the condensation in a vertical tube bundle condenser, in which case the product is conducted into the tubes and the vapor-side inlet into the tubes is flushed with a circulation stream, large in comparison to the amount of top draw, from the condensate collecting vessel associated with the condenser. A further suitable embodiment is to carry out the condensation in a tube bundle heat exchanger, in which case the product is conducted in the jacket region and the jacket region is flushed with a circulation stream from the condensate collecting vessel associated with the condenser. A particularly preferred embodiment of the closed condensation is the use of a direct condenser which, as the column section attached to the column in process step (e), is equipped with a total collecting cup, one or more liquid draws for pumped circulation, heat exchangers in the pumped circulation system to remove the heat of condensation and recycling of the cooled circulation stream into the column section. In a preferred embodiment E of the process according to the invention, the stream 11 contains from 1% by weight to 90% by weight, more preferably from 5 to 80% by weight, in particular from 10 to 60% by weight, of pentenenitriles.

In a further particularly preferred embodiment F, the specifications of embodiments D and E are attained.

In process step (f), a distillation of stream 10 takes place to obtain a stream 12 as the bottom product which comprises catalyst degradation products, the at least one promoter, adiponitrile and methylglutaronitrile, and a stream 13 comprising pentenenitriles as the top product.

The process step (f) may carried out in any suitable apparatus known to those skilled in the art. The distillation of process step (f) preferably takes place in one or more evaporator stages or one or more distillation columns. Useful internals for the distillation columns are preferably structured sheet metal packing, structured fabric packing, bubble-cap trays, dual-flow trays or beds of random packings or combinations of two or more of these classes of separating internals. The distillation column of process step (f) may be designed with one or more liquid or gaseous side draws. The distillation column from process step (f) may be designed as a dividing wall column having one or more gaseous or liquid side draws present.

The evaporator units for the one or more evaporator stages or one or more distillation columns may in particular be equipped with falling-film evaporators, thin-film evaporators, natural circulation evaporators, forced circulation-decompression evaporators and multiphase helical tube evaporators.

In a preferred embodiment of the process according to the invention, at least one of the evaporator stages of process step (f) is operated with a divided column bottom, in which case the circulation stream which is generally large relative to the bottom draw stream is conducted from a first column bottom of the evaporator stage in question to the evaporator, the liquid effluent stream from the evaporator is not returned directly to the column bottom, but rather collected in a second column bottom which is separated from the first column bottom, the bottom draw stream is obtained from the second column bottom and the remaining excess of evaporator circulation stream is allowed to overflow into the first column bottom, and the bottom draw stream obtained from the second column bottom is a mixture which is depleted in low boilers compared to the draw from the first column bottom.

The absolute pressure in process step (f) is preferably from 0.001 to 1.0 bar, more preferably from 0.005 to 0.1 bar, in particular from 0.01 to 0.05 bar. The distillation is carried out in such a way that the temperature in the bottom of the distillation apparatus is preferably from 40 to 250° C., more preferably from 50 to 200° C., in particular from 100 to 180° C. The distillation is carried out in such a way that the temperature at the top of the distillation apparatus is preferably from −15 to 150° C., more preferably from 0 to 60° C., in particular from 20 to 50° C. In a particularly preferred embodiment of the process according to the invention, the temperature ranges specified above are maintained both at the top and in the column bottom.

The content of pentenenitriles in stream 12 is preferably less than 10% by weight, more preferably less than 2% by weight, in particular less than 0.5% by weight.

The stream 13 obtained in process step (f) generally contains trans-3-pentenenitrile, cis-3-pentenenitrile, 4-pentenenitrile, trans-2-pentenenitrile, cis-2-pentenenitrile and (E)-2-methyl-2-butenenitrile. In a particularly preferred embodiment, this stream 13 is distilled at least partly to obtain a stream 22 depleted in trans-3-pentenenitrile, cis-3-pentenenitrile, 4-pentenenitrile, trans-2-pentenenitrile, cis-2-pentenenitrile and (E)-2-methyl-2-butenenitrile, and a stream 23 enriched in trans-3-pentenenitrile, cis-3-pentenenitrile, 4-pentenenitrile, trans-2-pentenenitrile, cis-2-pentenenitrile and (E)-2-methyl-2-butenenitrile in a further process step (I). The stream 22 depleted in cis-2-pentenenitrile and (E)-2-methyl-2-butenenitrile is preferably recycled into the hydrocyanation of process step (a).

In a particularly preferred embodiment of the process according to the invention, it is envisaged that both the stream 4 and the stream 13, if appropriate in the same apparatus from process step (i), are distilled to deplete in cis-2-pentenenitrile and (E)-2-methyl-2-butenenitrile. The resulting stream 19 depleted in cis-2-pentenenitrile and (E)-2-methyl-2-butenenitrile is, if appropriate, at least partly recycled into the hydrocyanation.

In process step (g), a distillation of stream 12 takes place to obtain a stream 14 as the bottom product comprising catalyst degradation products and the at least one promoter, and a stream 15 as the top product comprising adiponitrile and methylglutaronitrile.

Process step (g) may be carried out in any suitable apparatus known to those skilled in the art. The distillation of process step (g) more preferably takes place in one or more distillation columns. The columns may be equipped with one or more side draws. The internals used for the distillation columns are preferably structured sheet metal packings, structured fabric packings, bubble-cap trays, dual-flow trays or beds of random packings or combinations of two or more of these classes of separating internals.

The distillation of process step (g) more preferably takes place as an evaporation with one or more stages connected in series and condensation with the evaporators known per se to those skilled in the art. Examples of suitable evaporators for the one or more evaporator stages are falling-film evaporators, natural circulation evaporators, forced circulation-decompression evaporators, thin-film evaporators, short-path evaporators and multiphase helical tube evaporators. Particularly preferred evaporators are those which enable a very low evaporator surface temperature and a short contact time on the evaporator surface for the desired achievement of the degree of evaporation, and thus low thermal damage to the material to be concentrated. Suitable for this purpose are in particular falling-film evaporators, thin-film evaporators, multiphase helical tube evaporators and short-path evaporators.

The absolute pressure in process step (g) is preferably from 0.0001 to 0.5 bar, more preferably from 0.001 to 0.05 bar, in particular from 0.002 to 0.01 bar. The distillation is carried out in such a way that the temperature in the bottom of the distillation apparatus is preferably from 60 to 300° C., more preferably from 120 to 220° C., in particular from 140 to 180° C. The distillation is carried out in such a way that the temperature at the top of the distillation apparatus is preferably from 5 to 250° C., more preferably from 40 to 180° C., in particular from 60 to 120° C. In a particularly preferred embodiment of the process according to the invention, the aforementioned temperature ranges are maintained both at the top and in the bottom of the distillation apparatus.

In process stage (g), the stream 14 which comprises catalyst degradation products and the at least one promoter is removed. This stream is generally viscous, so that it has been found to be advantageous to make this stream more free-flowing by adding liquid. Suitable for this purpose is, for example, the methylglutaronitrile obtained in the downstream process step (h). In a particularly preferred embodiment of the present invention, process step (g) is thus performed as a two-stage distillation, by squeezing the stream 14 obtained in process step (g) in a subsequent process step (m) and diluting the squeezed stream 14 with at least a portion of the stream 17 obtained in process step (h) and comprising methylglutaronitrile. In a further preferred embodiment, the stream obtained in process step (m) is diluted with pentenenitrile isomers, more preferably with at least a portion of stream (19).

Additionally suitable as diluents for stream 14 are substances having higher boiling points than adiponitrile, as long as they increase the flowability.

Process step (m) may be carried out in any suitable apparatus known to those skilled in the art. Preference is given to thin-film evaporators, forced circulation-decompression evaporators or multiphase helical tube evaporators. Examples of suitable evaporators for the one or more evaporator stages are falling-film evaporators, natural circulation evaporators, forced circulation-decompression evaporators, thin-film evaporators, short-path evaporators and multiphase helical tube evaporators. Particularly preferred evaporators are those which, taking into account the viscosity of the material to be concentrated, enable a very low evaporator surface temperature and a short contact time on the evaporator surface for the desired achievement of the degree of evaporation, and thus low thermal damage to the material to be concentrated and minimized product of value losses. Suitable for this purpose are in particular falling-film evaporators, thin-film evaporators, multiphase helical tube evaporators and short-path evaporators.

The absolute pressure in process step (m) is preferably from 0.0001 to 0.5 bar, more preferably from 0.001 to 0.05 bar, in particular from 0.002 to 0.01 bar. The distillation is carried out in such a way that the temperature in the bottom of the distillation apparatus is preferably from 60 to 350° C., more preferably from 120 to 250° C., in particular from 160 to 220° C. In a particularly preferred embodiment, the pressure in process step (m) is set within the above-described range and simultaneously to less than in process step (g).

In process step (h), distillation of the stream 15 takes place to obtain a stream 16 comprising adiponitrile as the bottom product and a stream 17 comprising substantially methylglutaronitrile as the top product.

Process step (h) may be carried out in any suitable apparatus known to those skilled in the art. The distillation of process step (h) preferably takes place in one or more distillation columns. Useful internals for the distillation columns are preferably structured sheet metal packing, structured fabric packing, bubble-cap trays, dual-flow trays or beds of random packings or combinations thereof. The distillation column of process step (h) may be designed with one or more liquid or gaseous side draws. The distillation column from process step (h) may be designed as a dividing wall column having one or more gaseous or liquid side draws present.

The evaporator units for the one or more distillation columns may in particular be equipped with falling-film evaporators, thin-film evaporators, natural circulation evaporators, forced circulation-decompression evaporators and multiphase helical tube evaporators.

The absolute pressure in process step (h) is preferably from 0.0001 to 0.5 bar, more preferably from 0.005 to 0.06 bar, in particular from 0.01 to 0.03 bar. The distillation is carried out in such a way that the temperature in the bottom of the distillation apparatus is preferably from 60 to 300° C., more preferably from 120 to 220° C., in particular from 140 to 180° C. The distillation is carried out in such a way that the temperature at the top of the distillation apparatus is preferably from 40 to 250° C., more preferably from 60 to 180° C., in particular from 100 to 140° C. In a particularly preferred embodiment of the process according to the invention, the aforementioned temperature ranges are maintained both at the top and in the bottom of the distillation apparatus.

Should pentenenitriles still be present in stream 15, they may preferably be obtained via the top of the distillation column. In this case, the methylglutaronitrile stream 17 is obtained via a side draw of the column and adiponitrile via the bottom of the column.

In a further embodiment of the process according to the invention, the stream 16 comprising adiponitrile is obtained at a side draw. Preference is given to undertaking the withdrawal in the form of a gaseous side draw below the feed point. A mixture 23 is then obtained via the bottom and comprises substantially adiponitrile and high-boiling phosphorus-containing components which, despite low vapor pressure, get into stream 15 via process stage (g) and, where present, (m).

In a further embodiment of the process according to the invention, stream 17 comprising methylglutaronitrile is recycled into process step (e) as an intermediate boiler. In a further embodiment of the process according to the invention, stream 17 comprising methylglutaronitrile is recycled into process step (f) as an intermediate boiler. In a further particular embodiment, stream 17 comprising methylglutaronitrile is recycled simultaneously and fully or partly into process steps (e) and/or (f) as an intermediate boiler. The recycling of stream 17 into process steps (e) and/or (f) essentially achieves low bottom temperatures in process steps (e) and/or (f), so that any 3-pentenenitriles still present do not react with the promoter, for example zinc chloride.

In a further embodiment, other suitable medium boilers are recycled from the top or from a side draw of the column of process step (h) into process steps (e) and/or (f). Suitable substances do not form any vapor pressure minimum azeotropes with pentenenitriles or the extractant and its components, and, at the particular bottom temperatures of process steps (e) and/or (f), have a vapor pressure which is between that of the pentenenitriles and that of methylglutaronitrile, for example alkylphenols such as cresol isomers or tert-butylphenol, which are formed in traces in the process as degradation products of the catalyst components and are enriched in the top region of the columns of process step (h).

In a further embodiment of the process according to the invention, stream 17 comprising substantially methylglutaronitrile is used to dilute stream 14.

The adiponitrile obtainable by the above-described process has a purity which is characterized by the secondary components of preferably from 1 ppm by weight to 1% by weight, more preferably from 5 to 1000 ppm by weight, in particular from 10 to 500 ppm by weight, of methylglutaronitrile, and also preferably from 0.01 to 1000 ppm by weight of methylglutaronitrile, more preferably from 0.1 to 500 ppm by weight, in particular from 1 to 20 ppm by weight, of phosphorus compounds calculated as elemental phosphorus, detectable as the sum of volatile and involatile phosphorus compounds.

The methylglutaronitrile obtained by the above-described process has a purity of preferably from 50 to 100% by weight, more preferably from 80 to 99% by weight, in particular from 90 to 98% by weight, calculated as the sum of methylglutaronitrile and the isomeric ethylsuccinonitrile, the latter being obtained in parallel to methylglutaronitrile in the hydrocyanation and being virtually inseparable from methylglutaronitrile.

In the context of the present application, the term methylglutaronitrile always refers to methylglutaronitrile or a mixture of methylglutaronitrile and ethylsuccinonitrile.

Since the promoter has already been removed from adiponitrile and methylglutaronitrile in process step (g), it is not essential that the adiponitrile/methylglutaronitrile distillation is effected in apparatus made from chloride-resistant materials. When chloride-containing Lewis acids are used as the promoter, the design of the apparatus for process steps (e), (f), (g) and (m) entails the use of high-grade materials, wall coatings or other devices for protection against corrosion which are resistant to attack by chloride-containing media at the temperatures employed. The same applies to the use of bromide-containing promoters.

The invention is illustrated in detail hereinbelow with reference to a drawing and working examples.

FIG. 1 shows a particularly preferred embodiment of the process according to the invention.

In the reactor (1), a nickel(0) catalyst (cat), pentenenitriles (PN) which stem from a hydrocyanation of butadiene, and hydrogen cyanide (HCN) are fed in. Further constituents are 3-pentenenitriles and, if appropriate, extractant (EX) in stream 18 which are recycled in the process according to the invention. Over the nickel(0) catalyst, hydrocyanation of pentenenitriles with hydrogen cyanide takes place. The stream 1 resulting therefrom, which comprises pentenenitriles, the at least one catalyst, catalyst degradation products, the at least one promoter, extractant, adiponitrile and methylglutaronitrile from the hydrocyanation, is transferred to a distillation column (2).

There, a distillative removal of pentenenitriles and of extractant present via the top of the column takes place (stream 4). The bottom product (stream 3) of this distillation column comprises substantially the catalyst, catalyst degradation products, the at least one promoter, adiponitrile and methylglutaronitrile and is depleted in pentenenitriles.

The stream 4, obtained via the top of the distillation column (2), comprising pentenenitriles and the extractant present, is transferred to a further distillation column. There, the extractant is obtained as the top product and is used later for further extraction (stream 22). Pentenenitriles are obtained as the bottom product of this column (10) (stream 21). This bottom stream of pentenenitriles is subsequently transferred to a further column (9) in which a separation into 3-pentenenitrile (stream 18) and (E)-2-methyl-2-butenenitrile and cis-2-pentenenitrile (stream 19) is effected. The 3-pentenenitrile is recycled into the hydrocyanation of reactor (1) and may contain extractant (stream 18).

The bottom product of the distillation column (2) is subsequently transferred to an extraction column (stream 3). Here, an extraction of stream 3 is effected with an extractant to form a stream 6 which is drawn off via the top of the extraction column (3). This stream 6 is transferred to a further distillation column (4) in which a separation into a stream 8 as the bottom product which comprises the catalyst, and a top stream 9 which comprises the extractant is brought about. The thus obtained extractant of stream 9 is subsequently transferred to an extractant drying column (11) in which the dry extractant is withdrawn as the bottom product.

The stream 7 which stems from the distillation column (3) and is obtained as the bottom product in the distillation column (3) is subsequently transferred to a further distillation column (5).

In this distillation column (5) extractant still present is removed overhead as stream 11 and is likewise transferred to the extractant drying column (11).

The bottom product withdrawn from this column (5) is stream 10. This stream 10 is transferred to a further distillation column (6) in which the top product removed is a stream 13 which comprises pentenenitrile. This stream 13 is subsequently transferred to the distillation column (9).

The bottom product withdrawn from the distillation column (6) is stream 12 comprising catalyst degradation product, promoter, adiponitrile and methylglutaronitrile. This stream 12 is subsequently transferred to a further distillation column (7).

In this distillation column (7), the bottom product obtained is stream 14 which comprises nickel degradation products and the promoter.

The top product obtained from the distillation column is stream 15. Thereafter, stream 15 passes into a further distillation column (8) in which a separation into adiponitrile, stream 16, and methylbutanenitrile, stream 17, is effected.

WORKING EXAMPLES

In the examples, the following abbreviations are used:
HCN: hydrogen cyanide
T3PN: trans-3-pentenenitrile
C3PN: cis-3-pentenenitrile
4PN: 4-pentenenitrile
E2M2BN: (E)-2-methyl-2-butenenitrile
T2PN: trans-2-pentenenitrile
C2PN: cis-2-pentenenitrile
ADN: adiponitrile
MGN: methylglutaronitrile
VAN: valeronitrile
VCH: 4-vinylcyclohexene

Example 1

In example 1, a catalyst system based on nickel(0) complexes with a mixture of ligands is used for the hydrocyanation of butadiene. The ligand mixture for the hydrocyanation contains approx. 60 mol % of tri(m/p-tolyl) phosphite and 40 mol % of the chelate phosphonite 1:

In a loop reactor R1 of capacity 250 l which is equipped with a jet nozzle, impulse exchange tube, external pumped circulation and heat exchanger to remove the heat of reaction, the following streams are metered in:
(1) 10 kg/h of liquid, unstabilized hydrogen cyanide freed of water by distillation,
(2) 39 kg/h of pentenenitrile obtained from a process for preparing linear pentenenitrile according to DE-A-102 004 004 671, consisting of 97% in total of T3PN, C3PN and 4PN, and 2% E2M2BN,
(3) 25 kg/h of pentenenitrile obtained as stream 18 from column K9 from step (9), containing 81% in total of T3PN, C3PN, 4PN, and 3% T2PN, 1% C2PN and 3% E2M2BN.
(4) 6 kg/h of nickel(0) catalyst solution consisting of 40% ligand mixture, 2% nickel(0) and 3% ZnCl$_2$, prepared according to example 13 of DE-A-103 51 002.

The stream 1 drawn off from reactor R1 contains 40% in total of T3PN, C3PN and 4PN, and also 47% ADN and 6% MGN, corresponding to a conversion of 51% of pentenenitrile.

In step 2, stream 1 is fed to a distillation column K2 which is operated in stripping mode and is equipped with forced circulation-decompression evaporator, a top condenser and column internals having structured packing which generates 15 theoretical plates. The column K2 is operated at absolute top pressure 50 mbar, top temperature 313 K and bottom draw temperature 353 K.

Via the top of column K2 is obtained stream 4 (22 kg/h) which contains 81% in total of T3PN, C3PN and 4PN, and also 8% in total of T2PN and C2PN.

Via the bottom of column K2 are obtained 57 kg/h of a stream 3 having a content of 19% in total of T3PN, C3PN and 4PN, and also 1% in total of T2PN and C2PN. T2PN and C2PN are distinctly depleted relative to T3PN, C3PN and 4PN compared to the feed. Stream 3 additionally comprises the catalyst components nickel(0), the ligand mixture and ZnCl$_2$, and also catalyst degradation products.

In step (3), stream 3 is introduced at the lower end of a countercurrent extraction column K3 and extracted with 86 kg/h of stream 5 containing 93% methylcyclohexane and various pentenenitrile isomers. The stream 6 obtained at the top of the extraction consists of 91% extractant and contains, in addition to 4% in total of T3PN, C3PN and 4PN, the catalyst components nickel(0) and ligand mixture. The zinc chloride remains fully in the bottom draw of the extraction column in stream 7.

In step (4), stream 6 is conducted into a distillation column K4 which is equipped with falling-film evaporator, a divided column bottom and top condenser, and also column internals having structured packing which generate 12 theoretical plates. The column is operated at absolute top pressure 100 mbar, top temperature 308 K and bottom draw temperature 353 K. The reflux ratio is adjusted in such a way that 6% in total of T3PN, C3PN and 4PN are present in the top draw stream.

Via the top of column K4 is recovered the extractant which, together with a small makeup stream of pure methylcyclohexane dried to a water concentration below 10 ppm, is recycled as stream 9 into extraction column K3.

At the top of column K4, the extracted catalyst is obtained in stream 8 as a solution in pentenenitrile (13 kg/h). Stream 8 contains 18% ligand mixture, 1% Ni(0) and 68% in total of T3PN, C3PN and 4PN. The methylcyclohexane content in stream 8 is adjusted to 10 ppm by weight in stream 8 in column K4.

The catalyst-rich stream 8 is used in the hydrocyanation of butadiene to T3PN and 2M3BN.

In step (5), the stream 7 obtained in extraction column K3 is passed to a distillation column K5 which is operated in stripping mode and is equipped with forced circulation-decompression evaporator, at the top with a column section having total collecting cup, circulation and external heat removal as a direct condenser, and also column internals having structured packing which generate 5 theoretical plates. Column K5 is operated at absolute top pressure 180 mbar, top temperature 313 K and bottom draw temperature 453 K.

Via the top of column K5 is obtained stream 11 which is passed into distillation column K4. Stream 11 (22 kg/h) contains substantially 45% methylcyclohexane, 48% in total of T3PN, C3PN and 4PN, and also further pentenenitriles.

Via the bottom of column K5 is obtained stream 10 (45 kg/h) which also contains 5% in total of T3PN, C3PN and 4PN, and also 83% ADN and the MGN by-product and additionally catalyst degradation products together with $ZnCl_2$.

In step (7), stream 10 is worked up in an evaporator stage B7 which is equipped with forced circulation-decompression evaporator, top condenser and downstream thin-film evaporator B7a to concentrate the bottom product. The evaporator is operated at an absolute pressure of 5 mbar and bottom temperature 453 K.

Via the top of the evaporator B7 is drawn off as crude ADN stream 15 (44 kg/h) which also contains 5% in total of T3PN, C3PN and 4PN, and also 10% MGN.

Via the bottom of the thin-film evaporator B7a are obtained at bottom temperature 473 K concentrated catalyst residues together with the zinc chloride as stream 14, which are liquefied by admixing with 0.5 kg/h of MGN from the top of column K8 from step (8).

In step (8), stream 15 is conducted into a distillation column K8 which is equipped with thin-film evaporator, a top condenser operated as a partial condenser, and also column internals having structured packing which generate 25 theoretical plates. Column K8 is operated at an absolute pressure of 25 mbar of top pressure, top temperature 414 K and bottom draw temperature 453 K. The reflux ratio is suggested in such a way that 1% ADN is present in the top product. The amount of bottom draw of column K8 is controlled in such a way that the bottom product contains 100 ppm by weight of MGN.

Via the bottom of column K8 are obtained 37 kg/h of ADN as stream 16. At the top condenser of column K8 which is operated at 393 K, 3 kg/h of MGN are obtained in the liquid phase as stream 17 which is contaminated with 3PN, ADN and volatile catalyst decomposition products such as alkylphenols. The gaseous draw of the condenser of column K8 is condensed at 313 K in a postcondenser to obtain 4 kg/h of stream 20 which contains 54% in total of T3PN, C3PN and 4PN, and also 41% MGN.

In step (9), stream 4 from column K2 is worked up in distillation column K9 which is equipped with circulation evaporator, top condenser and column internals with structured packing which generate 35 theoretical plates. The column of step (9) is operated at an absolute pressure of 46 mbar of top pressure, top temperature 313 K and bottom draw temperature 338 K. The reflux ratio is adjusted in such a way that the top product still contains 0.5% T3PN.

Via the top of column K9 is obtained stream 19 (1.4 kg/h), which contains 65% C2PN and 29% E2M2BN, and also small amounts of VCH and VAN.

Via the bottom of column K9 is obtained stream 18 (25 kg/h) which contains 81% in total of T3PN, C3PN and 4PN, and also 3% T2PN, 1% C2PN and 3% E2M2BN. Stream 18 is recycled into reactor R1 as a recycle stream.

Example 2

In example 1, a catalyst system based on nickel(0) complexes with a mixture of ligands is used for the hydrocyanation of butadiene. The ligand mixture for the hydrocyanation contains approx. 80 mol % of tri(m/p-tolyl) phosphite and 20 mol % of the chelate phosphite 2:

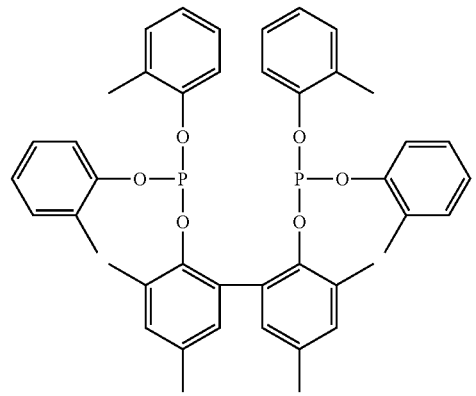

In a loop reactor R1 of capacity 250 l which is equipped with a jet nozzle, impulse exchange tube, external pumped circulation and heat exchanger to remove the heat of reaction, the following streams are metered in:
(1) 12 kg/h of liquid, unstabilized hydrogen cyanide freed of water by distillation,
(2) 39 kg/h of pentenenitrile obtained from a process for preparing linear pentenenitrile according to DE-A-102 004 004 671, consisting of 98% in total of T3PN, C3PN and 4PN, and 2% E2M2BN,
(3) 78 kg/h of pentenenitrile obtained as stream 18 from column K9 from step (9), containing 84% in total of T3PN, C3PN, 4PN, and 2% T2PN, 1% C2PN and 3% E2M2BN.
(4) 5 kg/h of nickel(0) catalyst solution consisting of 40% ligand mixture, 2% nickel(0) and 3% $ZnCl_2$, prepared according to example 4 of DE-A-103 51 002.

The stream 1 drawn off from reactor R1 contains 54% in total of T3PN, C3PN and 4PN, and also 34% ADN and 3% MGN, corresponding to a conversion of 35% of pentenenitrile.

In step 2, stream 1 is fed to an evaporator stage B2 which is equipped with falling-film evaporator und a top condenser. The evaporator stage B2 is operated at an absolute pressure of 20 mbar top pressure, top temperature 313 K and bottom draw temperature 343 K.

Via the top of the evaporator B2 is obtained stream 4 (64 kg/h) which contains 82% in total of T3PN, C3PN and 4PN, and also 5% in total of T2PN and C2PN.

Via the bottom of evaporator B2 are obtained 65 kg/h of stream 3 having a content of 19% in total of T3PN, C3PN and 4PN, and also 1% in total of T2PN and C2PN. Stream 3 additionally contains the catalyst components nickel(0), the ligand mixture and $ZnCl_2$, and also catalyst degradation products.

In step (3), stream 3 is introduced at the lower end of a countercurrent extraction column K3 and extracted with 97 kg/h of stream 5 containing 94% methylcyclohexane and various pentenenitrile isomers. The stream 6 obtained at the top of the extraction consists of 92% extractant and contains, in addition to 4% in total of T3PN, C3PN and 4PN, the catalyst components nickel(0) and ligand mixture. The zinc chloride remains fully in the bottom draw of the extraction column in stream 7.

In step (4), stream 6 is conducted into a distillation column K4 which is equipped with falling-film evaporator, a divided column bottom and top condenser, and also column internals having structured packing which generate 12 theoretical plates. The column is operated at absolute top pressure 125 mbar, top temperature 308 K and bottom draw temperature 361 K. The reflux ratio is adjusted in such a way that 5% in total of T3PN, C3PN and 4PN are present in the top draw stream.

In addition to stream 6, 3 kg/h of 3PN were metered to column K4, consisting of 98% in total of T3PN, C3PN and 4PN, and also small amounts of other pentenenitriles.

Via the top of column K4 is recovered the extractant which, together with a small makeup stream (10 g/h) of pure methylcyclohexane dried to a water concentration below 10 ppm to compensate for losses is recycled as stream 9 into extraction column K3.

At the bottom of column K4, the extracted catalyst in stream 8 is obtained as a solution in pentenenitrile (5 kg/h). Stream 8 contains 38% ligand mixture, 1% Ni(0) and 44% in total of T3PN, C3PN and 4PN. The methylcyclohexane content in stream 8 is adjusted in column K4 to 10 ppm by weight in stream 8.

In step (5), stream 7 obtained in extraction column K3 is conducted to a distillation column K5 which is equipped with forced circulation-decompression evaporator, divided column bottom, rectifying section and stripping section with column internals composed of structured packing which generate 9 theoretical plates. Column K5 is operated at an absolute pressure of 460 mbar of top pressure, top temperature 342 K and bottom draw temperature 433 K.

Via the top of column K5 is obtained a stream 11 which is conducted into distillation column K4. The reflux ratio of column K5 is adjusted in such a way that the top product consisting mainly of methylcyclohexane (87%) contains 5% T3PN.

Via the bottom of column K5 is obtained stream 10 (62 kg/h) which also contains 21% in total of T3PN, C3PN and 4PN, and also 70% ADN and the MGN by-product and additionally catalyst degradation products together with $ZnCl_2$ and nickel cyanides which are formed in the hydrocyanation in reactor R1.

In step (6), stream 10 obtained in extraction column K5 is conducted to a distillation column K6 which is equipped with forced circulation-decompression evaporator, divided column bottom and a rectifying section having column internals composed of structure packing which generate 4 theoretical plates. Column K6 is operated at an absolute pressure of 15 mbar of top pressure, top temperature 308 K and bottom draw temperature 426 K.

Via the top of column K6 is obtained stream 13 which is conducted into the distillation column K9 of step (9). The reflux ratio of column K6 is adjusted in such a way that the top product consisting mainly of pentenenitriles (93%) contains 100 ppm of MGN.

Via the bottom of column K6 is obtained stream 12 (62 kg/h) which also contains 1000 ppm in total of pentenenitriles, 89% ADN and 11% MGN by-product and additionally catalyst degradation products, $ZnCl_2$ and nickel cyanides.

In step (7), stream 12 is worked up in an evaporator stage B7 which is equipped with forced circulation-decompression evaporator, top condenser and downstream thin-film evaporator B7a to concentrate the bottom product. The evaporator is operated at an absolute pressure of 1 mbar and bottom temperature 365 K.

Via the top of evaporator B7 is drawn off as crude ADN stream 15 (49 kg/h) which, in addition to ADN, contains 0.1% in total of T3PN, C3PN and 4PN, and also 11% MGN.

Via the bottom of the thin-film evaporator B7a are obtained at 493 K concentrated catalyst residues together with zinc chloride as stream 14 (0.3 kg/h) which are liquefied by admixing with 0.1 kg/h of MGN from the top of column K7 from step (8).

In step (8), stream 15 is conducted into a distillation column K8 which is equipped with falling-film evaporator, top condenser and column internals having structured packing which generate 35 theoretical plates. Column K8 is operated at an absolute pressure of 7 mbar of top pressure, top temperature 393 K and bottom draw temperature 443 K. The reflux ratio is adjusted in such a way that the top product contains 0.10% ADN. The amount of top draw of column K8 is adjusted in such a way that the bottom product contains 50 ppm by weight of MGN.

In step (9), stream 4 from evaporator B2 is worked up in a distillation column K9 which is equipped with circulation evaporator, top condenser and column internals having structured packing which generate 35 theoretical plates. The column of step (9) is operated at an absolute pressure of 46 mbar of top pressure, top temperature 313 K and bottom draw temperature 338 K. The reflux ratio is adjusted in such a way that the top product still contains 500 ppm of T3PN.

Via the top of column K9 is obtained stream 19 (1.6 kg/h), which contains 66% C2PN and 29% E2M2BN, and also small amounts of VCH and VAN.

Via the bottom of column K9 is obtained stream 18 (78 kg/h) which contains 84% in total of T3PN, C3PN and 4PN, and also 2% T2PN, 1% C2PN and 3% E2M2BN. Stream 18 is recycled into reactor R1 as a recycle stream.

What is claimed is:

1. A process for preparing adiponitrile and methylglutaronitrile, characterized by the following process steps:
    (a) reacting a reactant stream comprising pentenenitriles with hydrogen cyanide in the presence of at least one catalyst and of at least one promoter to obtain a reaction stream which comprises pentenenitriles, the at least one nickel(0)-phosphorus ligand complex as a catalyst, catalyst degradation products, the at least one Lewis acid as a promoter, adiponitrile and methylglutaronitrile,
    (b) distilling the reaction stream to obtain a stream 3 which is depleted in pentenenitriles and comprises the at least one catalyst, catalyst degradation products, the at least one promoter, adiponitrile and methylglutaronitrile as the bottom product, and a stream 4 enriched in pentenenitriles as the top product,
    (c) extracting the stream 3 using an extractant which is selected from the group consisting of cyclohexane, methylcyclohexane, n-hexane, n-heptane, isomeric C6, C7, C8, C9 cycloaliphatics, isomeric C6, C7, C8, C9 isoaliphatics, cis-, trans-decahydronaphthalene and mixtures thereof present in stream 5 to obtain a stream 6 enriched with extractant as the top product which comprises the catalyst, and a stream 7 depleted in extractant as the bottom product which comprises catalyst degradation products, the at least one promoter, pentenenitriles, adiponitrile and methylglutaronitrile,
    (d) adding 3-pentenenitrile to the stream 6 to go into a distillation column, distilling the stream 6 to obtain a stream 8 comprising the catalyst as the bottom product and a stream 9 comprising the extractant as the top product,
    (e) distilling the stream 7 to obtain a stream 10 as the bottom product which comprises catalyst degradation products, the at least one promoter, pentenenitriles, adiponitrile and methylglutaronitrile, and a stream 11 comprising the extractant as the top product,
    (f) distilling the stream 10 to obtain a stream 12 as the bottom product which comprises catalyst degradation products, the at least one promoter, adiponitrile and methylglutaronitrile, and a stream 13 comprising pentenenitriles as the top product, wherein the stream 4 and/or the stream 13 enriched in pentenenitriles comprises cis-2-pentenenitrile and (E)-2-methyl-2-butenenitrile and is at least partly distilled to obtain a stream 18 depleted in cis-2-pentenenitrile and (E)-2-methyl-2-butenenitrile, and a stream 19 enriched in cis-2-pentenenitrile and (E)-2-methyl-2-butenenitrile, and the stream 18 is recycled at least partly into process step (a).

(g) distilling the stream 12 to obtain a stream 14 as the bottom product which comprises catalyst degradation products and the at least one promoter, and a stream 15 as the top product which comprises adiponitrile and methylglutaronitrile, (h) distilling the stream 15 to obtain a stream 16 comprising adiponitrile as the bottoms and a stream 17 comprising methylglutaronitrile as the top product.

2. The process according to claim 1, wherein the reactant stream stems from a homogeneous hydrocyanation of butadiene in the presence of a nickel (0) catalyst.

3. The process according to claim 1, wherein the extractant used is anhydrous.

4. The process according to claim 1, wherein stream 9 and/or stream 11 are recycled at least partly into process step (c).

5. The process according to claim 1, wherein process step (g) is performed as a two-stage distillation, by squeezing the stream 14 obtained in process step (g) in a subsequent process step (m) and diluting the squeezed stream 14 with at least a portion of the stream 17 obtained in process step (h) and comprising methylglutaronitrile.

6. The process according to claim 1, wherein the stream 9 obtained in process step (d) comprises less than 10% by weight of pentenenitriles.

7. The process according to claim 2, wherein the extractant used is anhydrous.

8. The process according to claim 3, wherein stream 9 and/or stream 11 are recycled at least partly into process step (c).

9. The process according to claim 2, wherein stream 9 and/or stream 11 are recycled at least partly into process step (c).

10. The process according to claim 4, wherein process step (g) is performed as a two-stage distillation, by squeezing the stream 14 obtained in process step (g) in a subsequent process step (m) and diluting the squeezed stream 14 with at least a portion of the stream 17 obtained in process step (h) and comprising methylglutaronitrile.

11. The process according to claim 3, wherein process step (g) is performed as a two-stage distillation, by squeezing the stream 14 obtained in process step (g) in a subsequent process step (m) and diluting the squeezed stream 14 with at least a portion of the stream 17 obtained in process step (h) and comprising methylglutaronitrile.

12. The process according to claim 2, wherein process step (g) is performed as a two-stage distillation, by squeezing the stream 14 obtained in process step (g) in a subsequent process step (m) and diluting the squeezed stream 14 with at least a portion of the stream 17 obtained in process step (h) and comprising methylglutaronitrile.

13. The process according to claim 5, wherein the stream 9 obtained in process step (d) comprises less than 10% by weight of pentenenitriles.

14. The process according to claim 4, wherein the stream 9 obtained in process step (d) comprises less than 10% by weight of pentenenitriles.

15. The process according to claim 3, wherein the stream 9 obtained in process step (d) comprises less than 10% by weight of pentenenitriles.

16. The process according to claim 2, wherein the stream 9 obtained in process step (d) comprises less than 10% by weight of pentenenitriles.

17. The process according to claim 1, wherein the catalyst in process step (a) is a zero valent nickel bidentate phosphorus complex.

* * * * *